United States Patent [19]

LeVahn et al.

[11] Patent Number: 4,949,707
[45] Date of Patent: * Aug. 21, 1990

[54] RETRACTOR APPARATUS

[75] Inventors: Bruce A. LeVahn, New Brighton; Robert E. Olson, Roseville, both of Minn.

[73] Assignee: Minnesota Scientific, Inc., Minneapolis, Minn.

[*] Notice: The portion of the term of this patent subsequent to Oct. 21, 2003 has been disclaimed.

[21] Appl. No.: 143,499

[22] Filed: Jan. 11, 1988

Related U.S. Application Data

[60] Continuation-in-part of Ser. No. 869,347, Jun. 2, 1986, Pat. No. 4,718,151, which is a division of Ser. No. 669,362, Nov. 8, 1984, Pat. No. 4,617,916.

[51] Int. Cl.$^5$ .............................................. A61B 17/02
[52] U.S. Cl. ...................................................... 128/20
[58] Field of Search .................. 128/20; 269/322, 328; 403/385; 24/535

[56] References Cited

U.S. PATENT DOCUMENTS

| | | | |
|---|---|---|---|
| 497,064 | 5/1893 | Van Meter | 128/20 |
| 1,049,642 | 1/1913 | Baesel | 24/136 R |
| 1,059,948 | 4/1913 | Neberle | 248/DIG. 4 |
| 1,168,574 | 1/1916 | Spurr | 128/20 |
| 1,198,186 | 9/1916 | Brown | 248/DIG. 4 |
| 1,230,873 | 6/1917 | Crossly | 128/20 |
| 1,382,783 | 6/1921 | Howard | 128/20 |
| 1,460,697 | 3/1922 | Bendlin | 128/20 |
| 1,707,689 | 4/1929 | Sloan | 128/20 |
| 1,747,799 | 2/1930 | Straus | 128/20 |
| 2,066,699 | 1/1937 | Skelton | 128/20 |
| 2,177,921 | 10/1939 | Zofrey | 74/242.8 |
| 2,469,904 | 5/1949 | Szubar | 248/124 |
| 2,557,430 | 6/1951 | Hensley | 148/102 |
| 2,586,488 | 2/1952 | Smith | 128/20 |
| 2,594,086 | 4/1952 | Smith | 128/20 |
| 2,623,517 | 12/1952 | Barlow | 128/20 |
| 2,670,731 | 3/1954 | Zoll et al. | 128/20 |
| 2,670,732 | 3/1954 | Nelson | 128/20 |
| 2,893,378 | 7/1959 | Cooper | 128/20 |
| 3,038,468 | 6/1962 | Raeuchle | 128/20 |
| 3,040,739 | 6/1962 | Grieshaber | 128/20 |
| 3,221,743 | 12/1965 | Thompson et al. | 128/303 |

(List continues on next page.)

FOREIGN PATENT DOCUMENTS

| | | |
|---|---|---|
| 460145 | 5/1928 | Fed. Rep. of Germany . |
| 1019217 | 1/1953 | France .................................. 128/20 |
| 1235185 | 5/1960 | France . |
| 446439 | 3/1949 | Italy . |

OTHER PUBLICATIONS

"Pilling Retractor Systems", four-page brochure of Narco Scientific Pilling Division, Fort Washington, Pa., dated 12/81.
"Thompson Retractor", two-page brochure of Richard C. Thompson, M. D., San Mateo, Calif.
"Bookwalter Retractor", two-page brochure of Codman & Shurtleff, Inc. Randolf, Mass.
King, W. B., "Use of Table-Fixed Abdominal Retractors", American Journal of Surgery, vol. 108, pp. 606–609, Nov. 1964.
Thompson, R. C. et al., "Mechanical Aids at the Operating Table", California Medicine, vol. 97, No. 1, pp. 28–30, Jul. 1962.
Price List of Automatic Retractor Holder of Great Eastern Lumber Co one page.

Primary Examiner—Edward M. Coven
Assistant Examiner—Mark S. Graham
Attorney, Agent, or Firm—Kinney & Lange

[57] ABSTRACT

A retractor apparatus includes an extension rod, first and second support rods and first and second clamps. The extension rod is attached to the first support rod with the first clamp. The first support rod is attached to the second support rod with the second clamp. The first and second support rods extend outwardly over the surgical table on opposite sides of the incision and the second support rod may be moved relative to the first support rod so as to correctly position the retractors over the incision.

14 Claims, 8 Drawing Sheets

U.S. PATENT DOCUMENTS

| | | | |
|---|---|---|---|
| 3,522,799 | 8/1970 | Gauthier | 128/20 |
| 3,572,326 | 3/1971 | Jenson | 128/20 |
| 3,638,973 | 2/1972 | Poletti | 128/20 |
| 3,749,088 | 7/1973 | Kohlmann | 128/20 |
| 3,810,462 | 4/1974 | Szpur | 128/20 |
| 3,823,709 | 7/1974 | McGuire | 128/20 |
| 3,858,578 | 1/1975 | Milo | 128/20 |
| 3,910,538 | 10/1975 | Baitella | 248/122 |
| 3,965,890 | 6/1976 | Gauthier | 128/20 |
| 3,998,217 | 12/1976 | Trumbull et al. | 128/20 |
| 4,010,741 | 3/1977 | Gauthier | 128/20 |
| 4,048,987 | 9/1977 | Hurson | 128/20 |
| 4,099,521 | 7/1978 | Nestor | 128/20 |
| 4,143,652 | 3/1979 | Meier et al. | 128/20 |
| 4,254,763 | 3/1981 | McCready et al. | 128/20 |
| 4,275,872 | 6/1981 | Mullis | 403/385 |
| 4,337,762 | 7/1982 | Gauthier | 128/20 |
| 4,355,631 | 10/1982 | LeVahn | 128/20 |
| 4,402,481 | 9/1983 | Sasaki | 248/276 |
| 4,421,107 | 12/1983 | Estes et al. | 128/20 |
| 4,421,108 | 12/1983 | Cabrera et al. | 128/20 |
| 4,443,128 | 4/1984 | Yamamoto et al. | 403/385 |

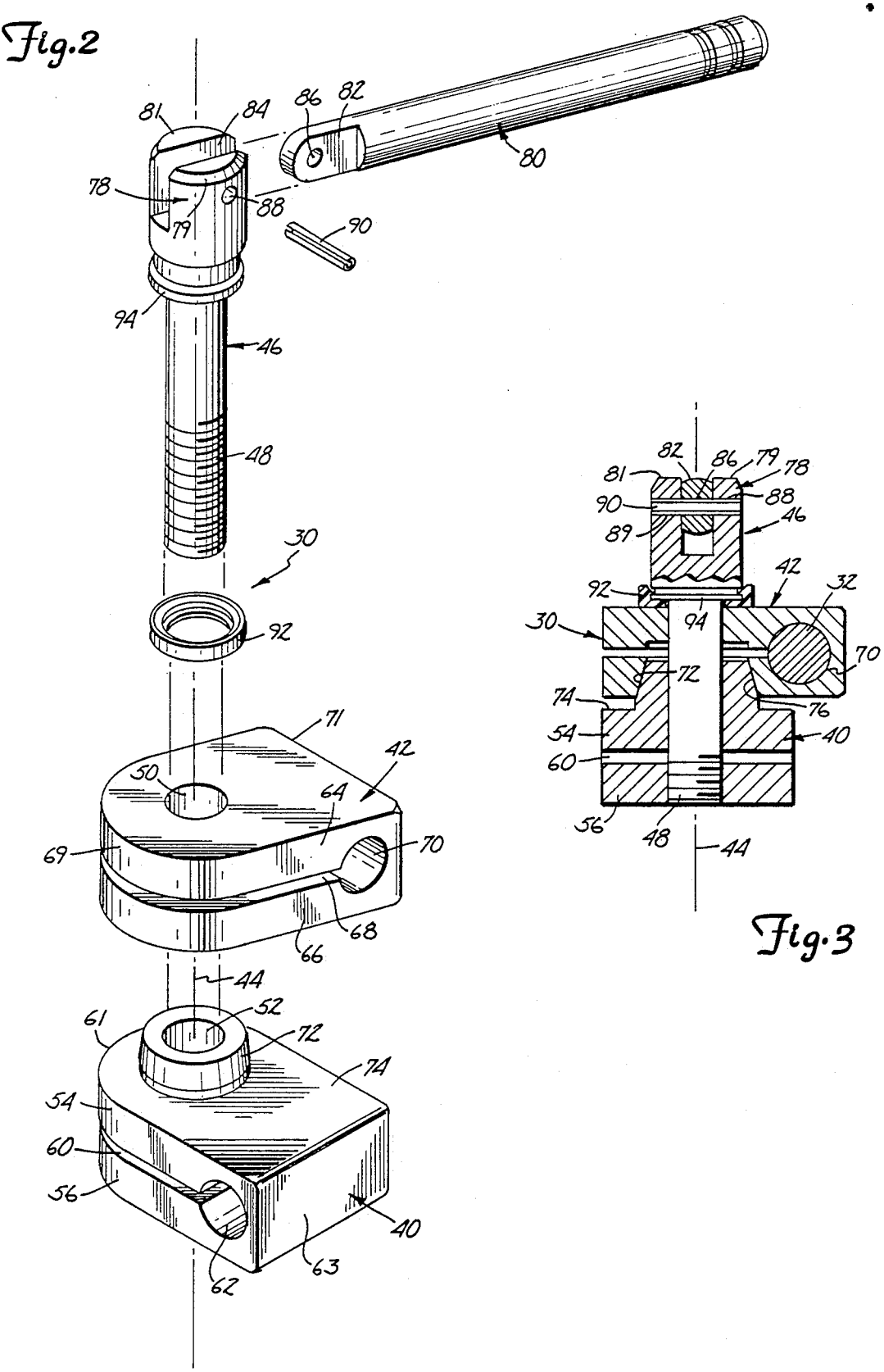

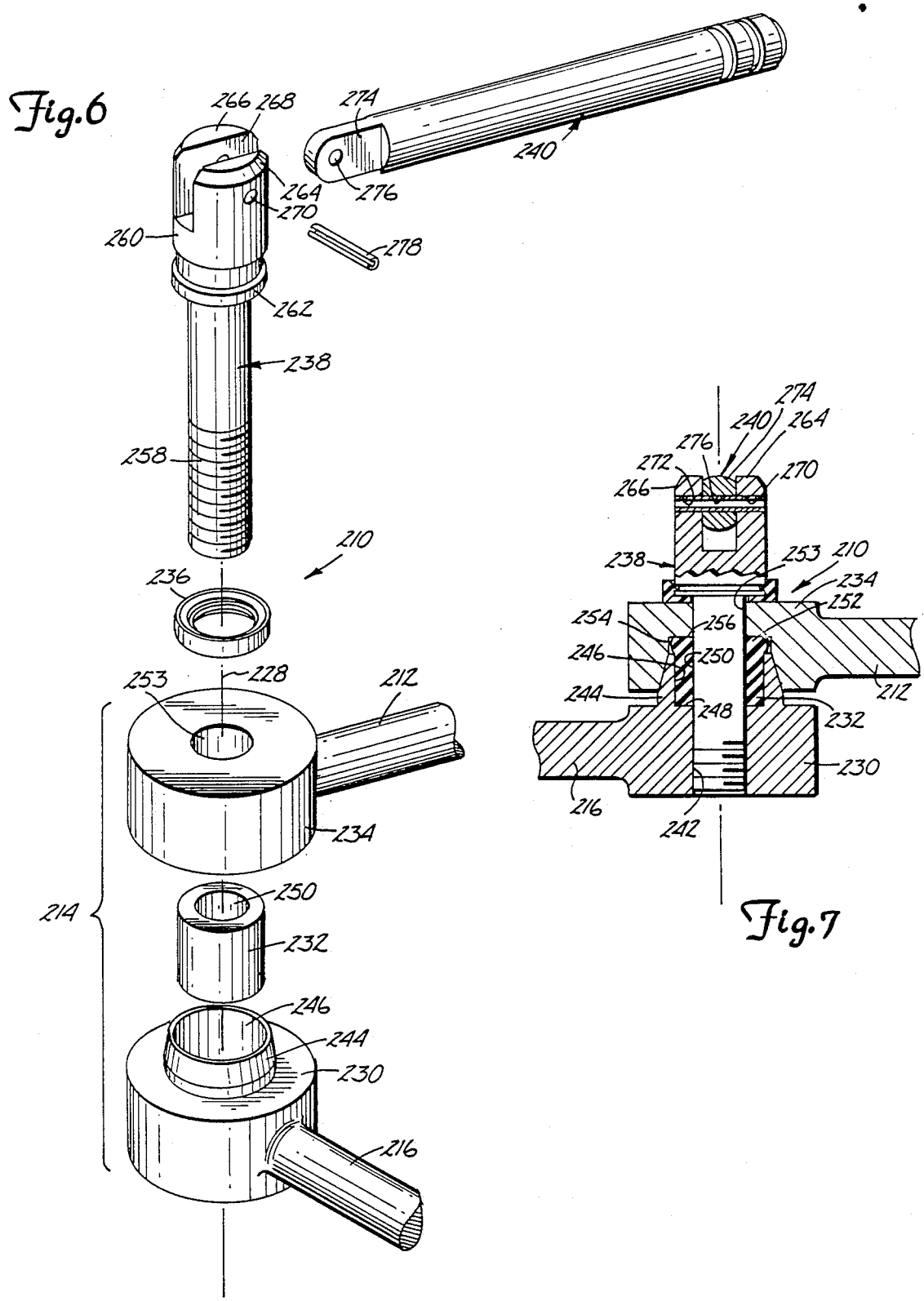

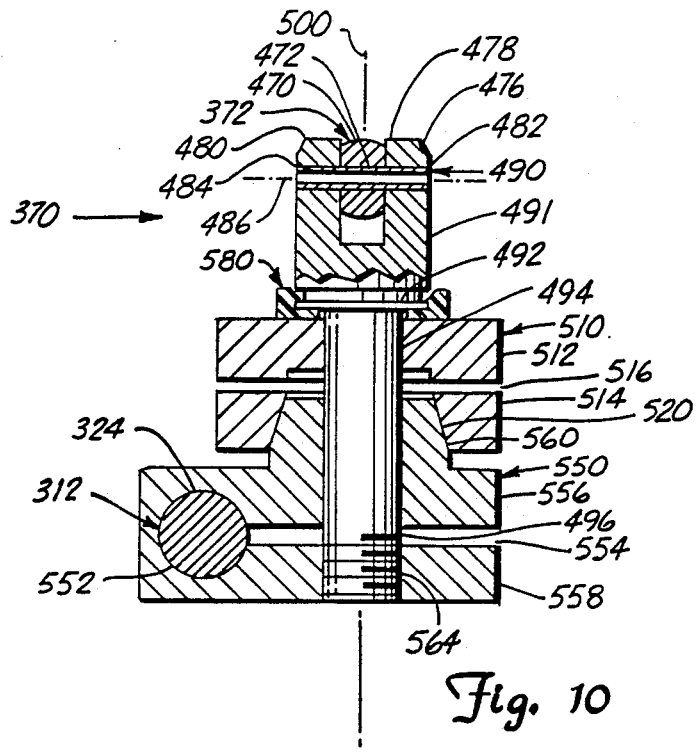
Fig. 10
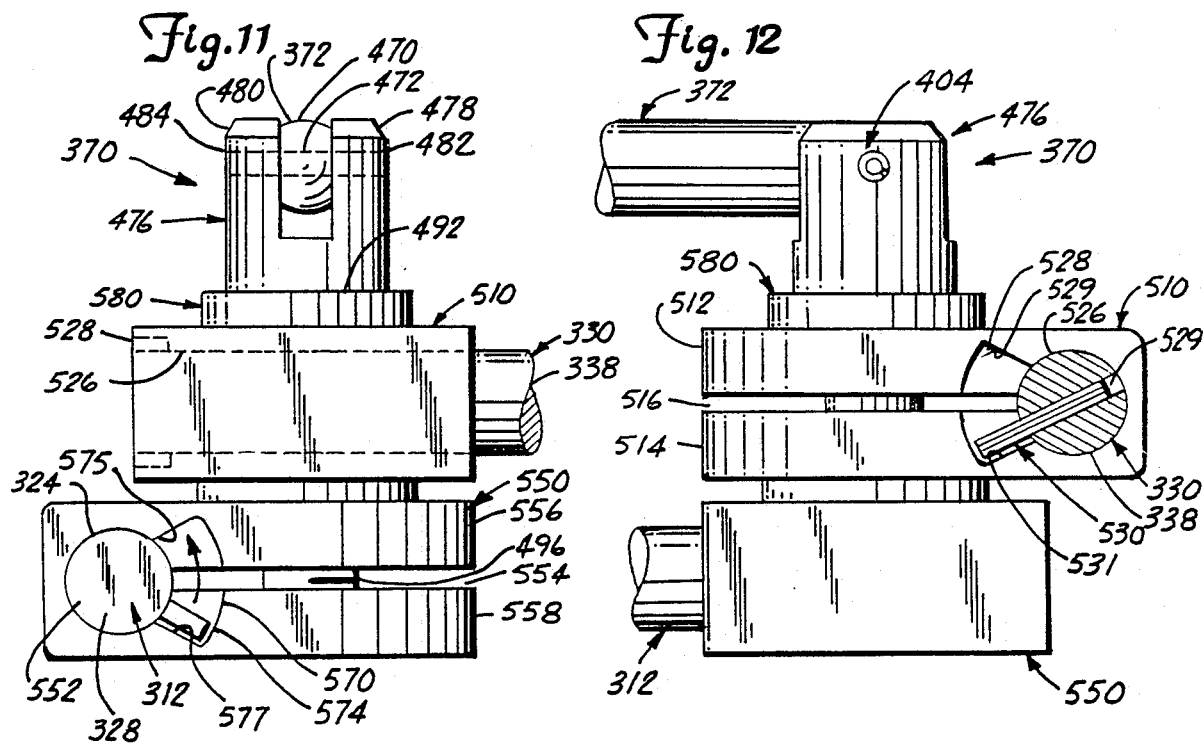
Fig. 11
Fig. 12

RETRACTOR APPARATUS

REFERENCE TO CO-PENDING APPLICATIONS

This application is a continuation-in-part of application Ser. No. 869,347 filed June 2, 1986, U.S. Pat. No. 4,718,151, which is a divisional application of application Ser. No. 669,362 filed Nov. 8, 1984, which issued into U.S. Pat. No. 4,617,916 on Oct. 21, 1986.

BACKGROUND OF THE INVENTION

1. Field of the Invention

The present invention relates to surgical retractor apparatus, and in particular, it relates to a retractor apparatus that is positionable to an area proximate an incision.

2. Description of the Prior Art

In abdominal and chest surgery, it is customary to use a retractor apparatus that is directly mounted to the operating table. The apparatus includes retractors that hold back tissue proximate to the surgical incision to enable the surgeon to work in areas such as the abdominal area or chest cavity.

Most retractor apparatus are positioned above a surgical drape that defines the sterile area where the surgeon and other attendants need to move to perform the surgery correctly and efficiently. The usefulness of any retractor apparatus is limited by the number of ways that the retractors can be positioned with respect to the incision of the body and with the ease and simplicity that the surgeon can adjust the relative position of the retractor before and during surgery. In addition, the retractor apparatus should not pose any great obstructions to the surgeon's movement during surgery or take up a great amount of space, limiting the movement of the surgeon and other attendants.

There have been many attempts in developing a suitable retractor apparatus For example, the following patents illustrate retractors and/or retractor support apparatus that are movable along a single plane:

| Inventor | U.S. Pat. No. |
|---|---|
| Sloan | 1,707,689 |
| Smith | 2,586,488 |
| Smith | 2,594,086 |
| Cooper | 2,893,378 |
| Raeuchie | 3,038,468 |
| Kohlman | 3,749,088 |
| Gauthier | 3,965,890 |
| Trumbull et al | 3,998,217 |
| Gauthier | 4,010,741 |
| Hursom | 4,048,987 |
| Gauthier | 4,337,762 |
| Estes et al | 4,421,107 |
| Cabrera | 4,421,108 |
| Country | Patent No. |
| Italy | 446,439 |

In addition, there are several patents and one brochure that illustrate devices and apparatus that permit pivotal movement of the retractor and/or some component of the apparatus about one axis with some also including movement along one plane:

| Inventor | U.S. Pat. No. |
|---|---|
| Van Meter | 497,064 |
| Spurr | 1,168,574 |
| Crossley | 1,230,873 |

-continued

| | |
|---|---|
| Barlow et al | 2,623,517 |
| Nelson | 2,670,732 |
| Grieshaber | 3,040,739 |
| Jensen | 3,572,326 |
| LeVahn | 4,355,631 |
| Country | Patent No. |
| Italy | 446,439 |
| Germany | 460,145 |

Brochures

"Pilling Retractor Systems", four-page brochure of Narco Scientific, Pilling Division, Fort Washington, Pa., dated 12/81.

There are also several patents, brochures and articles that either illustrate or discuss retractor apparatus that permit pivotal movement about two axes with some also permitting movement along a single plane:

| Inventor | U.S. Pat. No. |
|---|---|
| Nelson | 267,599 |
| Straus | 1,747,799 |
| Skelton | 2,066,699 |
| Zoll et al | 2,670,731 |
| Thompson et al | 3,221,743 |
| Szpur | 3,810,462 |
| McGuire | 3,823,709 |
| Baitella | 3,910,538 |
| Meier et al | 4,143,652 |
| McCready et al | 4,254,763 |
| Country | Patent No. |
| France | 1,235,185 |

Brochures

"Thompson Retractor," two-page brochure of Richard C. Thompson, M.D., San Mateo, Calif.

Price List of Automatic Retractor Holder of Great Eastern Lumber Company, Inc., New York, New York.

"Bookwalter Retractor," two-page brochure of Codman & Shurtleff, Inc., Randolph, Mass.

Articles

King, W. B., "Use of Table-Fixed Abdominal Retractors," *American Journal of Surgery,* Vol 108, pp. 606–609, November 1964.

Thompson, R. C. et al, "Mechanical Aids at the Operating Table," *California Medicine,* Vol. 97, No. 1, pp. 28–30, July 1962.

At least two prior art patents, the Milo U.S. Pat. No. 3,858,578 and the Poletti U.S. Pat. No. 3,638,973 disclose retractor arms that are movable through the use of ball joints Although ball joints provide a great degree of flexibility and movement, holding power and rigidity are sacrificed.

In many of the above prior art references, the surgeon does not have the ability to position the retractor universally, but is limited by the limited movement of retractor support apparatus. In addition, some of the developments in retractor apparatus in attempting to improve versatility in movement have sacrificed space and created obstructions for the surgeon

SUMMARY OF THE INVENTION

The present invention allows a surgeon to position retractor support rods proximate to an incision. The retractor apparatus includes an extension rod, first and second support rods and first and second clamps. The extension rod is attached to the first support rod with the first clamp. The first support rod is attached to the second support rod with the second clamp The first and second support rods extend outwardly over the surgical table on opposite sides of the incision and the second support rod may be moved relative to the first support rod so as to correctly position the retractors over the incision.

The retractor apparatus of the present invention permits a surgeon or one of his attendants to adjust the relative position of the retractors by moving a second support rod either closer or farther from the first support rod. The apparatus provides movable joints through the clamping mechanisms while also providing a joint that is exceptionally rigid, just as rigid as a support rod. The support apparatus does not require much space and provides little obstruction to the surgeon and attendants.

BRIEF DESCRIPTION OF THE DRAWINGS

FIG. 2 is an exploded perspective view of one clamping mechanism of the present invention.

FIG. 3 is a sectional view of the clamping mechanism of FIG. 2 with portions shown whole.

FIG. 6 is an exploded perspective view of a clamping mechanism of an auxiliary retractor support device of the present invention.

FIG. 7 is a sectional view of the clamping mechanism of the auxiliary retractor support device of FIG. 6 with portions shown whole.

FIG. 10 is a sectional view taken along the line 10—10 in FIG. 8 with portions shown whole.

FIG. 11 is a side view of the clamping mechanism of FIG. 10.

FIG. 12 is an end view of the clamping mechanism of FIG. 10 with portions shown in a sectional view.

DETAILED DESCRIPTION OF THE PREFERRED EMBODIMENTS

Figure 1:
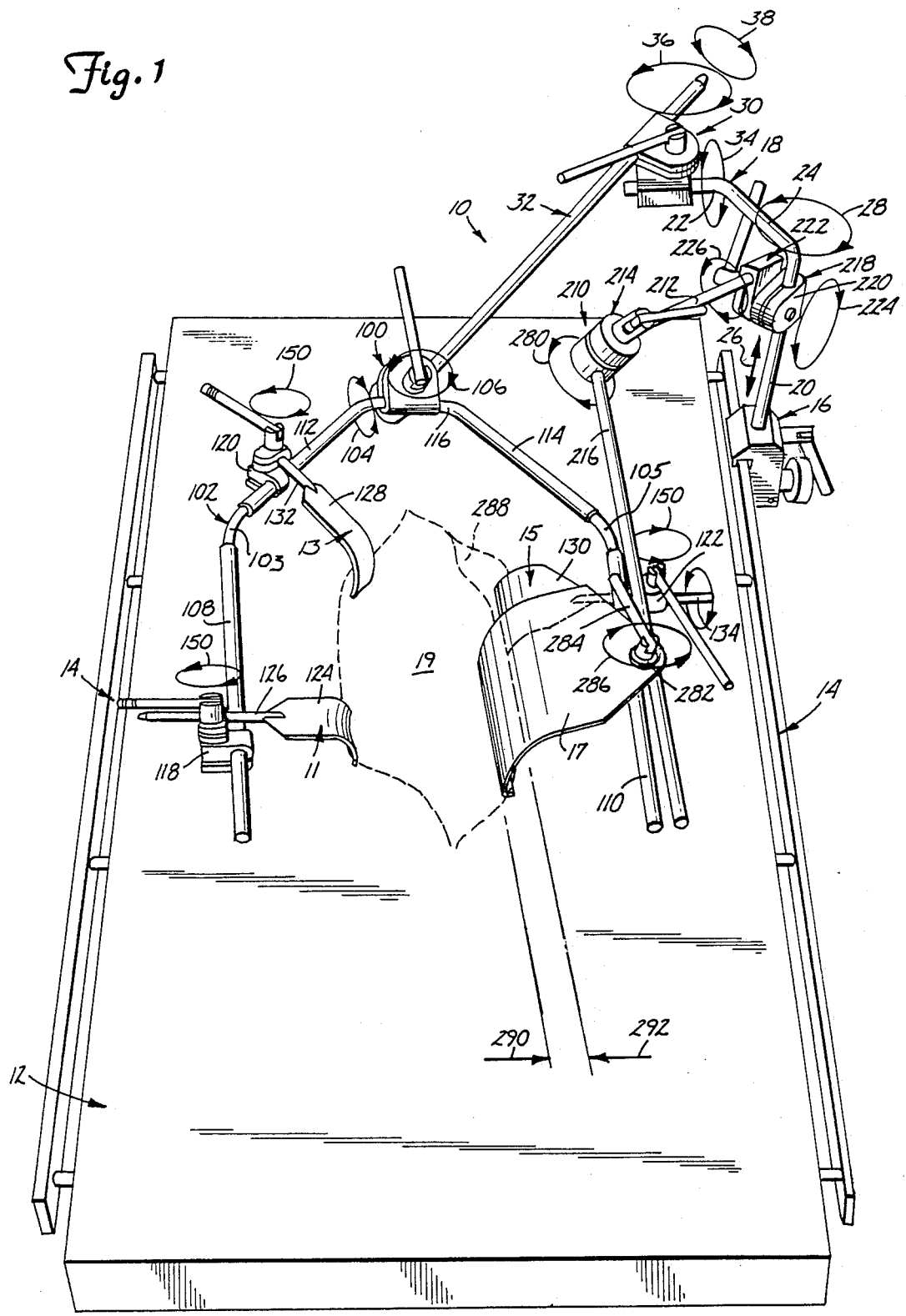
FIG. 1 is a perspective view of the retractor support apparatus of the present invention.

A retractor support apparatus of the present invention is generally indicated at 10 in FIG. 1. The retractor support apparatus 10 is used to support one or more retractors 11, 13, 15 and 17 above an operating table 12. The operating table 12 has side rails 14 to which retractor supports are commonly attached. The retractors are employed during major surgery, particularly of the chest or abdomen, and are applied to tissue proximate an area 19 of a surgical incision to hold back the cut tissue. Holding back the cut tissue exposes the area 19 in which the surgeon must work The retractor support apparatus of the present invention provides a novel support that is movable about at least three axes so that a surgeon can adjust the position of the retractors in a quick and efficient manner before or during surgery.

The support apparatus 10 includes a side rail clamping device 16 that clamps onto a side rail 14 of the operating table 12. The side rail clamping device 16 is described in U.S. Pat. No. 4,355,631 issued to the inventor as the present application and assigned to the same assignee of the present invention and is hereby incorporated by reference. The clamp 16 is used to connect primary support rod 18 to the railing 14. The support rod 18 has a lower substantially vertical section 20 and an upper substantially horizontal section 22 and preferably a midsection 24 disposed angularly with and connecting the lower and upper sections with each other. The lower section 20 insertably engages the clamp 16 so that when the clamp 16 is loosened, the support post 18 is movable in a substantially vertical direction as indicated by arrow 26 and is fixedly retained wih respect to rotation about the axis of the lower section 20.

A pivotal clamp 30 pivotally connects the upper section 22 of the support 18 with an extension rod 32. The extension rod 32 is retained in position in a rigid and fixed fashion, and when the clamp is released, the rod 32 is movable about three separate axes or has three degrees of freedom. First, the clamp 30 is rotatably movable about the axis of the upper section 22 of the support member 18, as indicated by arrows 34. Second, the clamp permits pivotal movement of the extension rod 32 about a pivotal axis running through the clamp as indicated by arrows 36. Third, the extension rod is rotatable about its own axis, as indicated by arrows 38. In addition, the rod 32 is movable along the axis of the upper section 22 and is movable along its own axis.

The clamp 30 is more fully illustrated in FIGS. 2 and 3. The clamp 30 includes a lower clamping section 40 and an upper clamping section 42 in a pivotal relationship about a pivot axis 44. A retaining bolt 46, having a lower threaded section 48, extends through a bore 50 of the upper clamping section 42 and into a threaded bore 52 in the lower clamping section 40.

The lower clamping section 40 is of a unitary construction, preferably machined from a single block of stainless steel, and has an upper and a lower leg 54 and 56 separated by a slot 60. The slot 60 extends from one end 61 of the clamping section 40 to a clamping bore 62 located proximate an opposite end 63. The clamping bore 62 receives and clamps a rod section, such as section 22, described with reference to FIG. 1. The legs 54 and 56 are resiliently movable with respect to each other such that the clamping bore 62 is reduced sufficiently in size to frictionally clamp the rod section.

Similarly, the upper clamping section 42 is of a unitary construction, preferably machined from a single piece of stainless steel, and includes an upper leg 64 and a lower leg 66, separated by a slot 68. The slot 68 extends from one end 69 of the clamping section to a clamping aperture 70 proximate an opposite end 71. The legs 64 and 66 are resiliently movable with respect to each other such that the clamping bore 62 is reduced sufficiently in size to clamp a rod, such as rod 32, as described with reference to FIG. 1.

The lower clamping section 40 has an upwardly-extending frusto-conical portion 72 on an upper surface 74 thereof for frictional engagement with a frusto-conical recess 76 disposed in the lower leg 66 of the upper clamping section 42. The aperture 52 is disposed substantially coaxially within the frusto-conical portion 72. The aperture 50 communicates with and is disposed substantially coaxially with respect to the frusto-conical recess 76. The frusto-conical portion 72 insertably engages the frusto-conical recess 76 so that the clamping section 40 and the clamping section 42 pivot about the axis 44 with the apertures 50 and 52 in substantial alignment.

The bolt 46 has a head portion 78 opposite from the threaded section 48. The head portion 78 has first and second upwardly extending retaining members 79 and 81 respectively, separated by a slot 84. The retaining members 79 and 81 have substantially aligned apertures 88 and 89, respectively. A handle 80 has a slot-engaging portion 82 that movably engages the slot 84 of the head portion 78. The slot-engaging portion 82 of the handle 80 has an aperture 86 extending therethrough that is alignable with an apertures 88 and 89. A spring pin 90 insertably engages the apertures 88, 86 and 89 to pivotally attach the handle 80 to the head portion 78. The handle 80 is pivotal about the pin 90 from one side of the bolt to another side of the bolt 46, approximately 180° to facilitate turning of the bolt 46.

A friction-reduction ring 92 is disposed between the upper clamping section 42 and the head portion 78 of the pin 46 The ring engages an annular flange 94 of the head portion 78 defining the lowermost section of the head portion 78. The ring 92 is made of a material that reduces friction between the flange 94 and the clamping section 42. One suitable material is sold under the trademark "DELRIN" by DuPont De Nemours & Co. of Wilmington, Del.

To operate the clamp 30, rods are inserted into the clamping bores 62 and 70 of the clamping sections 40 and 42, respectively, such as rod 32 and rod section 22, as illustrated in FIG. 1. The rod 32 and rod section 22 are pivotally moved about the axis 44 by pivoting the clamping sections 40 and 42 with respect to each other. The rod 32 is moved in a selected position within the bore 70 and the bore 62 is moved in a selected position on the rod section 22. The bolt 46 is then turned, preferably clockwise, moving the legs 54 and 56 toward each other, thereby frictionally retaining the rod in the bore 62, and moving the legs 64 and 66 toward each other frictionally retaining the rod in the bore 70, and frictionally binding the frusto-conical section 72 with the frusto-conical recess 76 such that the clamping sections 40 and 42 are restricted from movement with respect to each other. The frusto-conical section and frusto-conical recess provide a large area of metal to metal contact to securely retain the clamping section in a clamping position. The ring 92, being made of a low friction material, helps to turn the bolt 46 more tightly and therefore increasing the clamping force of the clamping sections 40 and 42.

To loosen the clamp 30, the handle 80 is simply turned in an opposite direction, almost immediately releasing the clamping sections 40 and 42 from frictional engagement and permitting the legs 54 and 56 and legs 64 and 66 to move away from each other releasing the rods within the bores 62 and 70, all respectively. It will be appreciated that by simply turning the bolt 46 the rod 32 and anything attached to the rod 32 is quickly and easily positioned about three axes and retained in position and is quickly and easily released from position for further movement.

A second pivotal clamp 100 connects a retractor support rod 102 with the extension rod 32. The clamp 100 has the same structure as the clamp 30, described above with reference to FIG. 2. The clamp 100 permits pivoting of the retractor support rod 102 about the axis of the extension rod 32 as indicated by arrows 38, and about an axis of a midsection 116 of the retractor support rod 102 and about a pivotal axis of the clamp as indicated by arrows 106.

The retractor support rod 102 has preferably two spaced apart legs 108 and 110 which have angularly disposed sections 112 and 114, respectively, that are angularly disposed towards each other and connected by the midsection 116. The legs 108 and 110 are spaced sufficiently apart so that the legs are arranged on either side of the area 19 with sufficient room to position the retractors 11, 13, and 15.

It will be appreciated that the retractor support rod 102 is quickly positionable by operating either clamp 16, 30 or 100 or any combination of the three. The retractor support rod 102 can be raised vertically and moved horizontally as indicated by arrow 28 by operation of clamp 16. The support rod 102 can be inclined, with respect to the horizontal, toward one end or the other end of the operating table by operation of clamp 30 or 100 or both. In addition, operation of clamps 30 and 100 permit the support rod 102 to be tilted towards the left or the right side of the operating table. The retractor support rod 102 is also movable along the longitudinal axis of the operating table by adjusting the position of the extension rod 32 and the support post 18 and operation of clamps 16, 30 and 100.

The retractors 11, 13 and 15 are pivotally attached to the retractor support by retractor clamps 118, 120 and 122. The retractor clamps provide three degrees of freedom in positioning each of the retractors. The retractor 11 includes a retractor blade 124 and a retractor handle 126 attached to the blade and insertably engaging the clamp 118. Similarly, the retractors 13 and 15 have blades 128 and 130, and handles 132 and 134, which are inserted into clamps 120,122, all respectively.

The support rod 102 has corner portions 103 and 105 of reduced diameter, that is, a diameter smaller than that of sections 108, 112, 114 and 110. The corner portions 103 and 105 have a diameter sufficiently smaller than the adjacent sections 108 and 112 and adjacent sections 110 and 114 so that the retractor clamps are movable between sections 108 and 112, and 110 and 114 by only slightly loosening the clamp so that it is movable along the rod sections 108, 112, 114 and 110. The reduced diameter of the corner portions permits movement of slightly loosened clamps between rod sections.

Figures 4, 5:
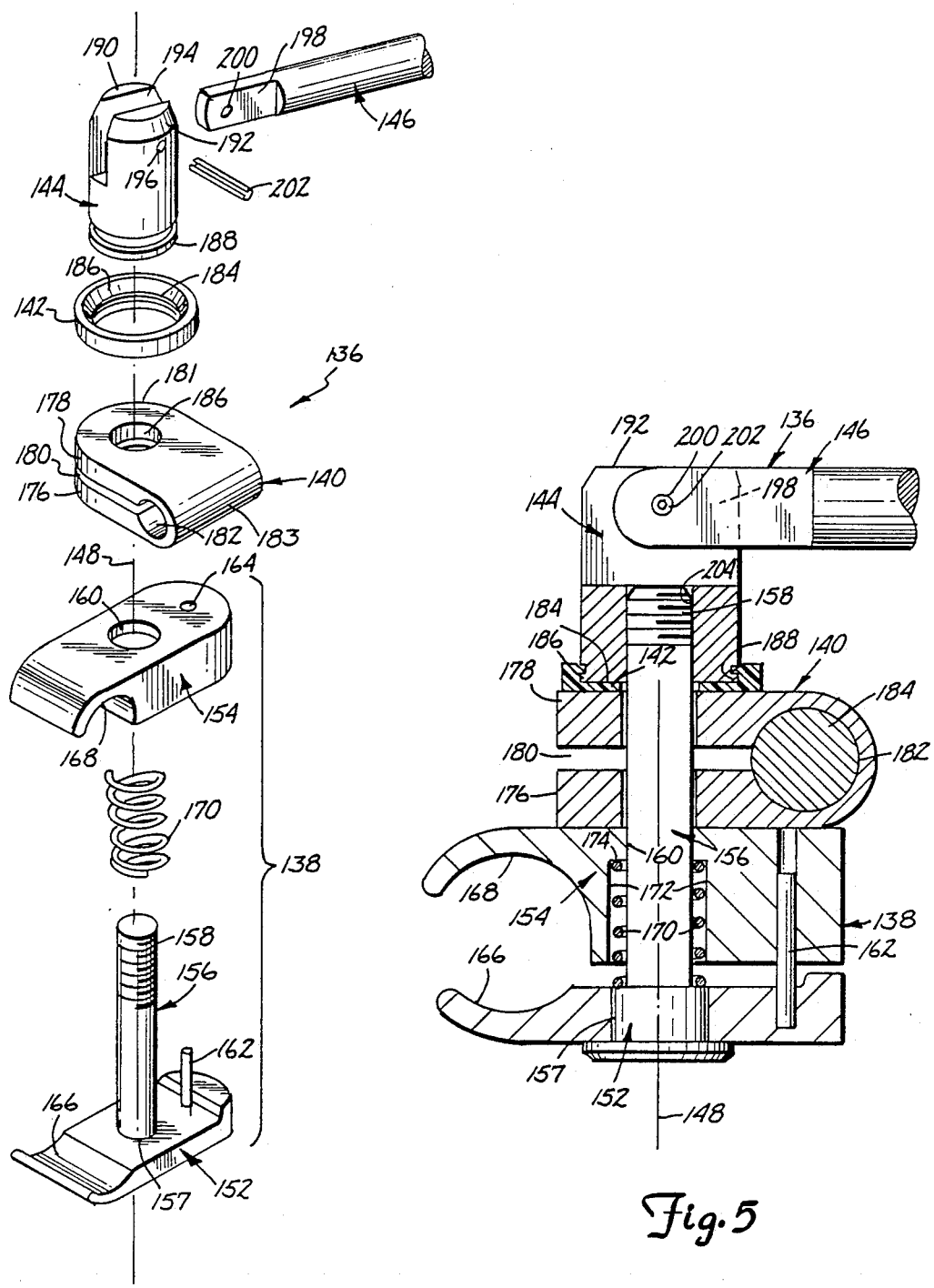
FIG. 4 is an exploded perspective view of a retractor clamping mechanism of the present invention.
FIG. 5 is a sectional view of the retractor clamping mechanism of FIG. 4 with portions shown whole.

The clamps 118, 120 and 122 are of similar construction and are described collectively with reference to a clamp 136 illustrated in FIGS. 4 and 5. The clamp 136 includes a lower clamping section 138, an upper clamping section 140, a friction-reduction ring 142, a head section 144 and a handle 146. The lower clamping section, the upper clamping section, ring 142 and head section 144 are disposed coaxially about an axis 148 The axis 148 is considered the pivot axis about which the retractor is pivoted, as indicated by arrows 150 in FIG. 1.

The lower clamping section 138, as illustrated in FIGS. 4 and 5, includes a lower clamping jaw 152 and an upper clamping jaw 154. A bolt 156 extends upwardly through an aperture 157 in the lower clamping jaw 152. The bolt 156 has a threaded upper end 158 and is coaxially disposed on the axis 148 and extends through an aperture 160 of the upper clamping jaw 154. A pin 162 fixedly attached to the lower jaw 152 also extends upwardly and through a bore 164 in the upper clamping jaw 154. The pin 162 and bolt 156 cooperate to retain the upper and lower clamping jaws 152 and 154 in clamping alignment with each other.

The lower clamping jaw 152 has a lower clamping groove 166 and the upper clamping jaw has an upper clamping groove 168 facing the lower clamping groove 166. The lower clamping groove 166 and the upper clamping groove 168 are aligned along their longitudinal axis, as best illustrated in FIG. 5, for clamping the retractor support rod 102, as illustrated in FIG. 1.

A coil spring 170 is coaxially disposed about the bolt 156. The coil spring, at a lower end, abuts against an upper surface of the clamping plate 152 and extends into a downwardly facing bore 172 of the upper clamping plate 154. The bore 172 is disposed coaxially with respect to the bore 160 and the axis 148 and forms a downwardly facing shoulder 174 against which the spring 170 abuts at an upper end. The spring 170 provides a force to separate the lower and upper clamping sections 152 and 154 from a clamping position.

The upper clamping section 140 includes a lower clamping leg 176 and an upper clamping leg 178 separated by a slot 180 that extends from an end 181 of the upper clamping section up to a retractor handle clamping groove 182 located proximate an opposite end 183. The upper clamping section 140 is of a unitary construction, preferably machined from a single block of stainless steel. The legs 176 and 178 are resiliently movable with respect to each other such that the clamping bore 182 is reduced sufficiently in size to frictionally clamp a retractor handle 184. The retractor handle 184 represents retractor handles 126, 132 and 134, as illustrated in FIG. 1.

The upper clamping section 140 also includes a bore 186 coaxially disposed about the axis 148 and through which the bolt 156 extends. When a force is applied such that the legs 176 and 178 are pushed towards each other, the clamping groove 182 clamps around the handle 184 of the retractor securing the retractor in a fixed position.

The friction-reduction ring 142 abuts against an upper surface of the upper clamping section 140. The ring 142 includes an annular shoulder 184 whose outer periphery is defined by an annular wall 186. The head section 144 has a lower annular flange portion 188 that engages the annular shoulder 184 of the ring 142 with the wall 186 engaging sides of the flange 188. The head section 144 includes spaced apart upwardly extending handle retaining members 190 and 192 separated by a slot 194, as best illustrated in FIG. 4. A pin receiving bore 196 extends through the retaining member 192 and is in alignment with another pin receiving bore (not shown) extending through retaining member 190.

The handle 146 includes a slot engaging portion 198 that movably engages the slot 194. The slot engaging portion 198 includes a third pin receiving bore 200 that is alignable with the first pin receiving bore 196 and the second pin receiving bore in the member 190 (not shown). A spring pin 202 engages the bore 196, the bore 200 and the bore (not shown) in the member 190 such that the handle 146 pivots about the pin 202 within the slot 194. The handle 146 is pivotable approximately 180° from a substantially horizontal position on one side of the head section 144 to an opposite side of the head section 144 to facilitate the operation of the retractor clamp regardless of the relative position of the handle 146.

The head section 144 includes a downwardly facing bolt engaging threaded bore 204 that is coaxially aligned with the bore 186 of the upper clamping section and the aperture bore of the upper clamping jaw 154 such that the bolt 156 extends through the bore 160, the bore 186 and into the bore 204, threadably engaging said bore 204.

When the head section 144 is turned clockwise by grasping the handle 146, the lower clamping jaw 152 and the upper clamping jaw 154 are moved towards each other against the force of the spring 170 and the clamping legs 176 and 178 of the upper clamping section 140 are also moved towards each other substantially simultaneously clamping a retractor handle positioned within the clamping grooves 166 and 168 and the retractor support rod 184 in the clamping bore 182. To release the retractor from a clamping position within the clamping grooves 166 and 168 and to release the clamp from the retractor support rod 184, the handle is turned in the opposite direction, turning the head 144 with the spring 170 acting to separate the upper and lower clamping jaws 152 and 154 and the legs 176 and 178 separating due to the resilient force within the clamping section 140.

As is easily understood by those skilled in the art from the discussion above, the retractor support apparatus requires very little space. Any obstruction to the surgeon or the other attendants by the support apparatus is minimal. Although the apparatus takes up a minimal amount of space, the support apparatus is a very rigid and durable structure primarily due to the clamping mechanisms 30 and 100. The frusto-conical section and recess provide a retaining force that includes a large area of metal to metal contact. Once the metal to metal contact is established, clamps 30 and 100 cannot be moved from their selected positions by any force normally found in the operating room, such as a surgeon or attendant leaning or bumping against the apparatus. The retractor support rod 102, since it is a rod and not a flat plate, provides minimum obstruction to the surgeon working in the area 19. However, due to the structure of clamps 30 and 100, the retractor support rod 102 is held in a sufficiently rigid fashion that is capable of withstanding contact by the surgeon and other attendants while retaining the position that had been previously selected.

An auxiliary retractor support device 210 is also illustrated in FIG. 1. The auxiliary retractor support device includes a first support rod section 212, a clamping section 214 and a second retractor support rod section 216. The auxiliary retractor support device is secured to the support rod 18 proximate a free end of the first rod section 212 by a clamp 218. The clamp 218 is of a similar structure as the clamp 30 illustrated in FIGS. 2 and 3. The clamp 218 also provides three degrees of freedom for positioning the retractor support device 210 about three separate axes. First, the clamp 218 and the retractor device 210 are pivotable about an axis running through the support rod 18, as indicated by the arrows 28. Second, the clamp 218, like the clamp 30, has a first clamping section 220 and a second clamping section 222 which are pivotable about an axis generally indicated by the arrows 224. The auxiliary retractor support device 210 is pivotable about the axis indicated by arrows 224 when the clamping section 222 is moved with respect to the clamping section 220. Third, the retractor support device is pivotable about the axis of the rod section 212, as indicated by arrows 226 when the rod section 212 is rotated within the clamping bore of the clamping section 222. In addition, the device 210 is movable along the support rod 18 and along the axis of the rod section 212.

The clamping device 210 is more fully illustrated in FIGS. 6 and 7. The clamping device 210 permits pivoting of the rod sections 212 and 216 about an axis 228 running through the clamping section 214. The clamping section 214 includes a lower clamping member 230, a resilient bushing 232 and an upper clamping member 234. The clamping device also includes a friction-reduction ring 236, a turning bolt 238 for bringing the clamping members 230 and 234 in clamping relationship, and a handle 240 for turning the bolt 238.

The rod section 216 is preferably permanently attached to the lower clamping member 230. The lower clamping member 230 includes an upwardly facing threaded bolt receiving bore 242 for receiving the bolt 238 in threaded cooperation. The lower clamping section includes an upwardly extending frusto-conical portion 244 in coaxial alignment with the bore 242. The frusto-conical portion 244 includes a bushing retaining bore 246 in substantially coaxial alignment with the bore 244. The bore 244 has a lower shoulder 248 for supporting the bushing 232. The bushing 232 has a bolt receiving bore 250 disposed coaxially along the axis 228. The bushing 232 is positioned within the bore 246 and rests on the shoulder 248. The bushing 232 has an upper portion 252 that extends above the frusto-conical portion 244. The bushing 232 is made of a resilient material, such as a medical grade rubber that can be sterilized, and provides a force to separate the clamping members 230 and 234 from the clamping position.

The upper clamping member 234 includes a bore 253 and downwardly facing frusto-conical recess 254, both coaxially aligned along the axis 228. The frusto-conical recess has an upper shoulder 256 that defines the upper limit of the recess and engages the top of the bushing 232. The bushing 232 acting against the shoulder 248 and the shoulder 256 provides a force to separate the lower clamping member 230 from the upper clamping member 234.

The turning bolt 238 has a lower threaded section 258 and an upper head section 260. The turning bolt 238 extends through the ring 236, through the bore 253 of the upper clamping member 234, through the bore 250 of the bushing, and into the bore 242 for threaded engagement. The head section 260 of the turning bolt 238 includes a lower annular flange portion 262 that engages the ring 236. The ring 236 is made of a low friction material, such as "DELRIN". The head section 260 includes first and second handle retaining members 264 and 266 separated by a slot 268. A pin retaining bore 270 extends through the member 264 and a second pin retaining bore 272 extends through the member 262, as best illustrated in FIG. 7.

The handle 240 includes a slot engaging portion 274 that movably engages the slot 268 and includes a third pin engaging bore 276 that is aligned with the bores 270 and 272. A spring pin 278 engages the bore 270, 276 and 272 such that the handle is pivotal approximately from a horizontal position on one side of the turn bolt 238 to an opposite side of the turn bolt 238 or approximatey 180°.

When the turn bolt 238 is turned by turning the handle 240 in a clockwise direction, the upper and lower clamping members 234 and 230 are forced together by the threaded engagement of the bolt with the bore 242, moving the bolt through the bore 242. The frusto-conical section 244 and frusto-conical recess 254 frictionally engage each other and retain the members 234 and 230 in a clamping position. When the handle 240 is turned in an opposite direction, the force of the resilient bushing 232 separates the members 230 and 234 moving the clamping device 210 from the clamping position.

Referring back to FIG. 1, the clamping device 210 permits movement of the retractor support rod section 216 about the axis of the clamping device as indicated by arrows 280. The device 210 is used as an auxiliary support alone or in combination with the support rod 102. As illustrated in FIG. 1, the device 210 is positioned so that the rod section 216 runs substantially parallel to the leg 110 of the rod 102. The retractor 17 is mounted to the rod section 216 so that it can be used in cooperation with the retractor 15 mounted on the leg 110 of the rod 102.

The retractor 17 includes a clamping section 282 that clamps the retractor onto the rod section 216 by turning handle 284. The clamping section 282 also permits pivoting of the retractor 17, as indicated by arrow 286, about an axis running through the clamping section 282.

The retractor 15 and the retractor 17 are used in combination to hold back different layers of tissue. The retractor 15 retains a first layer of tissue 288. The retractor 17 is spaced from the retractor 15, as indicated by arrows 290 and 292. The use of the auxiliary device 210 provides the additional flexibility in being able to position the retractor 17 independently from the retractor 15. The device 210 provides versatility since the rod section 216 is positionable independently of the leg 110 of the rod 102. It will be understood that a separate support post, similar to the support post 18, can be clamped to the rail 14 on an opposite side of the table 12 so that the rod section 216 can be positioned along the leg 108. Furthermore, the rod section 216 can be positioned with respect to either sections 112 and 114 of the rod 102 so that a retractor clamp thereon can be used in association with the retractor 13.

Figure 8:
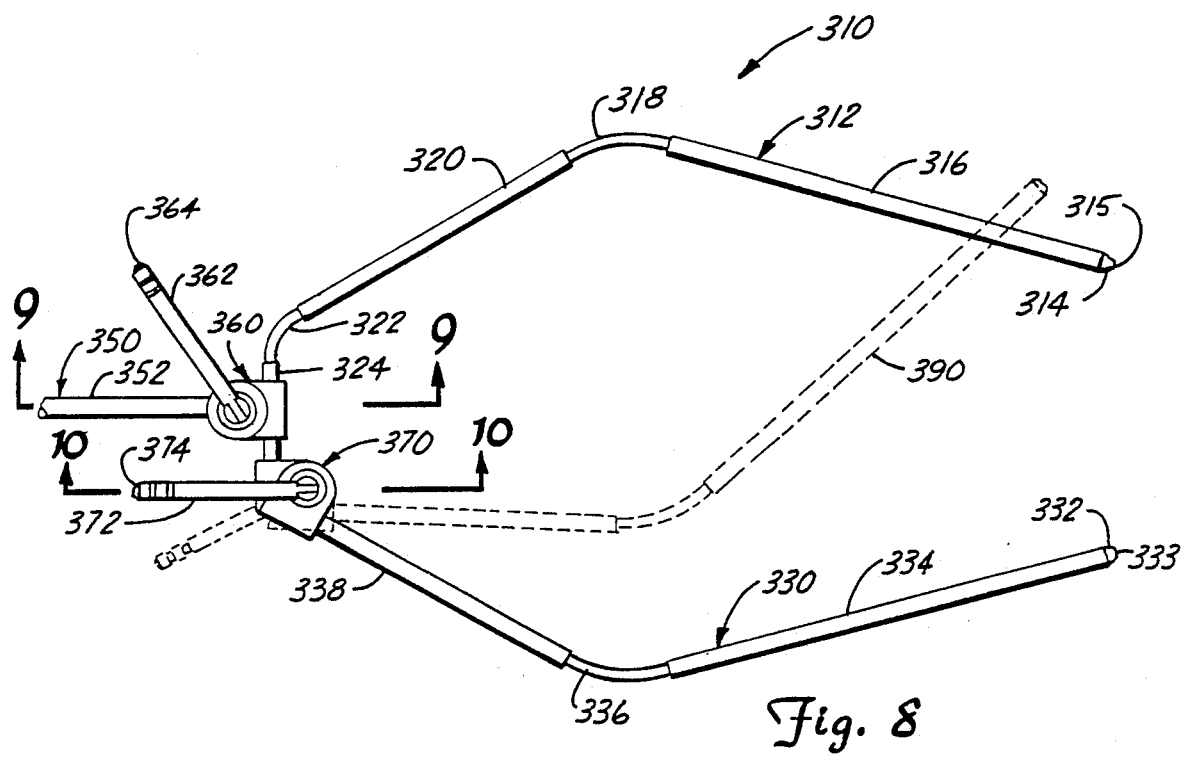
FIG. 8 is a top view of an alternative embodiment.

An alternative embodiment of the present invention, an adjustable wishbone-type retractor support apparatus, is generally indicated at 310 in FIG. 8. The embodiment 310 has a first support rod 312. The first support rod 312 has a tapered end 314 with a blunt point 315, a first substantially linear portion 316, and a first curved portion or elbow 318 having a reduced diameter. The first support rod 312 also has a second or middle substantially linear portion 320, a second elbow or curved portion 322 having a reduced diameter and a third substantially linear or end portion 324.

The embodiment also includes a second support rod 330. The second support rod 330 has a tapered end 332 with a blunt point 333, a substantially linear portion 334, a single elbow or curved portion 336 having a reduced diameter, and a second substantially linear or end portion 338.

Figure 9:
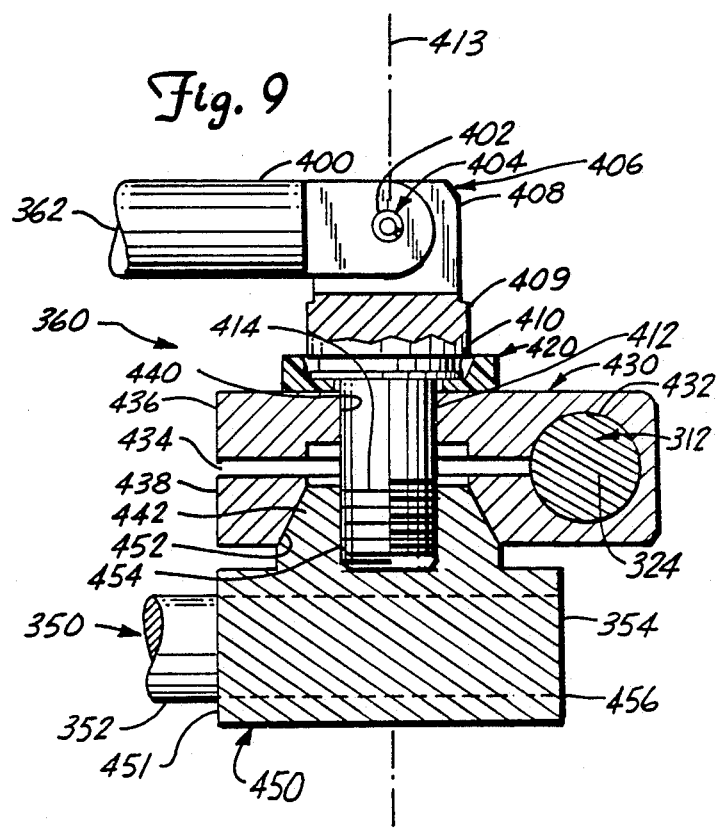
FIG. 9 is a sectional view taken along the line 9—9 in FIG. 8.

The embodiment further includes an extension rod 350. The extension rod has a leg 352 with an end portion 354, as illustrated in FIG. 9, which is connected to the third substantially linear portion 324 of the first support rod 312 through a first clamp 360. The first clamp 360 is actuated by a handle 362 which also terminates in a blunt end 364.

The third substantially linear portion 324 of the first support rod 312 is also connected to the second substantially linear portion 338 of the second support rod 330 by a second clamp 370. The second clamp 370 has a handle 372 having a blunt end 374.

The first clamp 360 and the second clamp 370 are located on the third substantially linear portion 324 of the first support arm 312 such that the first clamp 360 lies between the second clamp 370 and the second elbow or curved portion 322.

When released, the second clamp 370 allows for alteration of the angular relationship between the third substantially linear portion 324 of the first support arm 312 and the second substantially linear portion 338 of the second support arm 330. In FIG. 8, an altered angular relationship between the first support arm 312 and the second support arm 330 as indicated by broken lines 390.

As illustrated in FIG. 9, the clamp 360 includes a first clamp handle 362 with a handle connecting end 400. The handle connecting end 400 has a pin receiving aperture 402 disposed generally perpendicular to the axis of the handle 362. A pivot pin 404 extends through the aperture 402.

A turning bolt 406 includes a bolt head 409 having a handle retaining member 408. The combination of the pivot pin 404 and the rounded end 403 allows handle 362 to pivot approximately 180° on the turning bolt 406 about the pivot pin 404. Depending from the bolt head 409, the turning bolt 406 has a radially extending flange or shoulder 410 and a shank portion 412 terminating in a threaded shank portion 414. The shank portions 412 and 414 lie generally along aixs 413.

The first clamp 360 includes a first clamping section or upper clamp body 430. The first clamping section 430 is a unitary body and has a first clamping bore 432 located proximate one end of the first clamping section 430. The clamping bore 432 has a diameter approximately equivalent to the diameter of the third substantially linear portion 324 of the first support rod 312.

A slot 434 extends radially from the clamping bore 432 and across the unitary body of the first clamping section 430 generally opposite the proximate end. The slot 434 defines an upper resilient leg 436 and a lower resilient leg 438 of the first clamping section 430. The upper and lower resilient legs 436 and 438 tend to reduce the diameter of the first clamping bore 432 when they are squeezed together. Squeezing upper and lower resilient legs 436 and 438 together and thus reducing the diameter of the first clamping bore 432 serves to frictionally clamp the third substantially linear portion 324 of the first support rod 312.

The lower resilient leg 438 also includes a female or recessed frusto-conical surface 442. The female or recessed frusto-conical surface 442 of the lower resilient leg 438 shares the axis 413 with an aperture 440 in the upper resilient leg 436. The aperture 440 has a diameter sufficient to allow the threaded portion 414 and the shank portion 412 but not the shoulder 410 of the bolt 406 to pass through.

The first clamp 360 also includes a clamp base 450. The clamp base 450 has a generally cylindrical outer surface 451. A bore 456 extends radially through the base 451. Within the bore 456 the end 354 of the extension rod 350 is attached and preferably permanently locked. A male frusto-conical surface 452 extends outwardly from the clamp base 450 along the axis 413. A threaded recess 454 is disposed along the axis 413 frusto-conical surface 452 for threadably engaging the threaded shank portion 414. The male frusto-conical surface 452 is configured to cooperate with the female frusto-conical surface 442 of the first clamping section 430 to frictionally engage the surface 442.

In use, as the turning bolt 406 is turned and thereby drawn further into the threaded recess 454, upper and lower resilient legs 436 and 438 are drawn or squeezed together, thereby reducing the radius of the first clamping bore 432 and thus frictionally clamping or locking the third substantially linear portion 324 of the first support rod 312 within the first clamping bore 432. Simultaneously, the female frusto-conical surface 442 frictionally engages the male frusto-conical surface 452 such that the angular relationship of the clamp base 450 is fixed or frictionally clamped with respect to the first clamping section 430, thereby also fixing the angular relationship between the third substantially linear portion 324 of the first support rod 312 and extension rod 350 about the pivot axis 413.

The first clamp 360 may be further refined. For example, as turning bolt 406 is rotated and drawn into threaded portion 454, the radial shoulder 410 engages the upper resilient leg 436, forcing it closer to the lower resilient leg 438. In a specially preferred embodiment, a friction-reduction ring 420 disposed between the bolt radial shoulder 410 and the upper resilient leg 436 reduces friction thereby making rotation of the turning bolt 406 easier and more effective in applying pressure within the clamp 360. The ring 420 is made of a material that reduces friction between the shoulder 410 and the upper leg 436. One suitable material is sold under the trademark "DELRIN" by DuPont DeNemours & Co. of Wilmington, Del.

The second clamp handle 372 has a handle end portion 470 that includes a pin receiving aperture 472 as illustrated in FIG. 10. A turning bolt 476 includes two handle receiving members 478 and 480 on a bolt head 491. The handle receiving members 478 and 480 are spaced apart to allow the handle end portion 470 to be positioned between the members 478 and 480. The handle retaining members 478 and 480 each have a pin receiving aperture 482 and 484 which are disposed about a common pivot axis 486. When the handle end portion 470 is placed between the handle retaining members 478 and 480 such that the pin receiving aperture 472 of the handle end 470 shares the common pivot axis 486, and a pivot pin 490 connects the three apertures 472, 482 and 484, the second clamp handle 372 is pivotable approximately 180° to the turning bolt 476 about the common pivot axis 486. The turning bolt 476 also includes a radially extending flange or shoulder 492 depending from the bolt head 491, followed by a shank portion 494 and terminates in a threaded end portion 496. The turning bolt 476 rotates about an axis 500.

The second clamp also includes an upper unitary clamping body member 510 having an upper resilient leg 512 and a lower resilient leg 514 separated by a slot 516. The upper resilient leg 512 has an aperture 518 of diameter approximately equal to the diameter of the shank portion 494 of the turning bolt 476. The lower resilient leg 514 has a recessed or female frusto-conical surface 520 disposed about the axis 500 as the aperture 518 of the upper resilient leg 512.

The second clamp 370 also includes a lower clamping member 550. The lower clamping member 550 has a clamping bore 552 proximate one end of the lower clamping member 550. A slot 554 extends radially from the clamping bore 552 to an opposite end of the lower clamping member 550. The slot 554 defines an upper resilient leg 556 and a lower resilient leg 558.

The clamping bore 552 has a diameter approximately equivalent to the third substantially linear portion 324 of the first support rod 312. When the third substantially linear portion 324 of the first support rod 312 is inserted within the clamping bore 552 and upper resilient leg 556 is forced closer to lower resilient leg 558, the diameter of clamping bore 552 is slightly reduced. Reducing the diameter of the clamping bore 552 provides a frictional clamping action upon the third substantially linear portion 324 of the first support rod 312.

A male or protruding frusto-conical surface 560 extends outwardly from the upper resilient leg 556, perpendicularly to the slot 554. The male frusto-conical surface 560 is configured to mate with the female frusto-conical surface 520 of the lower resilient leg 514 of the upper clamping member 510. Coaxially disposed with the frusto-conical surface 560 is a pivot bore or aperture 562 having a diameter approximately equal to the diameter of the shank 494 of the turning bolt 476. The lower resilient leg 558 has a threaded aperture or pivot bore 564 generally disposed about the axis 500 as the pivot bore 562 of the upper resilient leg 556. The proportions of the threaded aperture 564 are such that they generally match the threaded end portion 496 of the turning bolt 476.

In use, rotation of the turning bolt 576 about its longitudinal axis 500 such that bolt 576 is drawn further within threaded aperture 564 applies a force squeezing the upper resilient leg 512 closer to the lower resilient leg 514 of the upper clamping member 510 and squeezing lower resilient leg 558 closer to the upper resilient leg 556 of the lower clamping member 550 and further squeezing the male frusto-conical surface 560 tightly against the female frusto-conical surface 520. When this tightening or clamping action occurs, shoulder 492 of turning bolt 476 is forced against the upper resilient leg 512 of the upper clamping member. In an especially preferred embodiment, a friction-reduction ring 580 is interposed between the shoulder 492 of the turning bolt 476 and the upper resilient leg 512 of the upper clamping member 510. The friction-reduction ring 580 is preferably formed of friction reducing material. A suitable material is sold under the trademark "DELRIN" by DuPont DeNemours & Co. of Wilmington, Del.

Rotation of the turning bolt 476 about the axis 500 is facilitated by applying a tangential force to the handle 372. Such a force is most effective when the handle 372 is at right angles to the axis 500. The spaced apart arrangement of the handle receiving members 478 and 480 effectively translates this force into rotation of the turning bolt 476. A combination of the handle 372 and the friction-reduction ring 580 allows the bolt 476 to be drawn further within the threaded aperture 564, thus applying a tremendous squeezing force to the clamp 370.

As illustrated in FIG. 11, the third substantially linear portion 324 has an end surface 328 and a protruding notch or pin 574 extending radially from the third substantially linear portion 324, proximate to the end surface 328. The protruding notch or pin 574 fits within a fan-shaped recess 570 disposed within the lower clamping body 550. The fan-shaped recess extends generally radially from the clamping bore 552 in the same general direction as the slot 554, such that the protruding notch or pin 574 is engageable within the fan-shaped recess 570.

Rotation of the third substantially linear portion 324 within the clamping bore 552 is limited to the rotation allowed between stop shoulders 575 and 577 which define the arc angle of the fan-shaped recess 570. When the protruding notch or pin 574 is fitted within the fan-shaped recess 570 and the first support rod 312 is locked in a stationary position through the use of the first clamp 360, the second clamp 370 may only rotate about clamping bore 552 within the limits defined by the stop shoulders 575 and 577.

The upper clamping body 510 also includes a clamping aperture or bore 526 with a radially extending fan-shaped recess 528 having stop shoulders 529 and 531 as illustrated in FIG. 12. The clamping bore 526 has a diameter approximately equal to the second substantially linear portion 338 of the second support rod 330.

Disposed within the clamping bore 526 is the second substantially linear portion 338 of the second support rod 330. The second substantially linear portion 338 includes a pin receiving aperture 529 extending therethrough. The aperture 529 partly contains a protruding pin 530 having a length longer than the diameter of the second substantially linear portion 338 and a radius generally equivalent to the pin receiving aperture 529. The pin 530 extends from the bore 529 at a substantially right angle from the second end portion 338 and is engageable within the recess 528. In combination, the protruding pin 530 and the fan-shaped recess 528 serve to limit the rotation of the second substantially linear portion 338 within the bore 526.

In a similar manner to that described for the lower clamping body 550, the upper and lower resilient legs 512 and 514 when forced closer together, narrow the slot 516 and slightly reduce the diameter of the clamping bore 526. Reducing the diameter of bore 526 causes a frictional clamping action against the second substantially linear portion 338 of the second support rod 330. Thus, the three clamping bores 432, 526 and 552 all function similarly.

Figure 13:
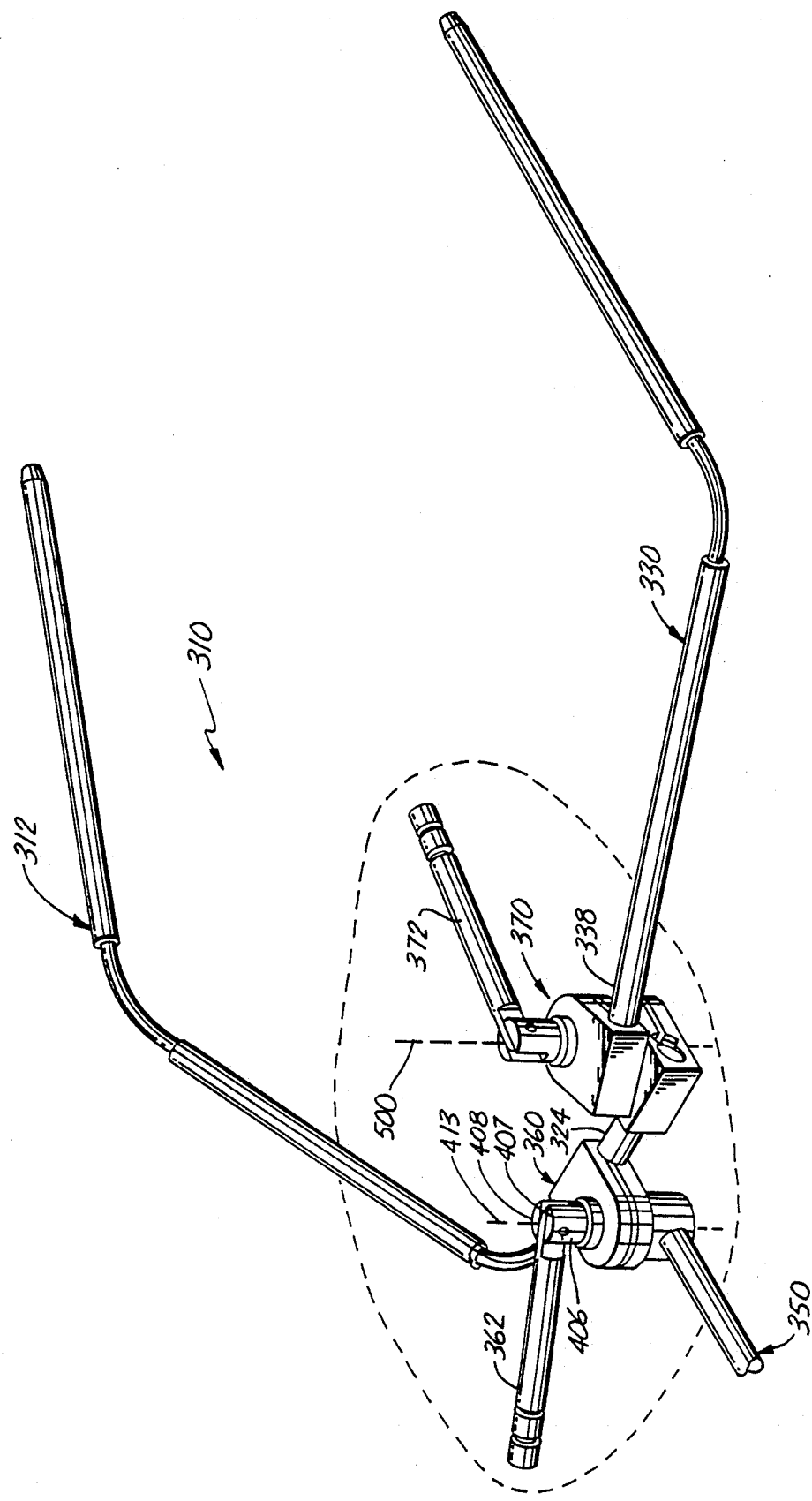
FIG. 13 is a perspective view of the embodiment of FIG. 8.
Figure 14:
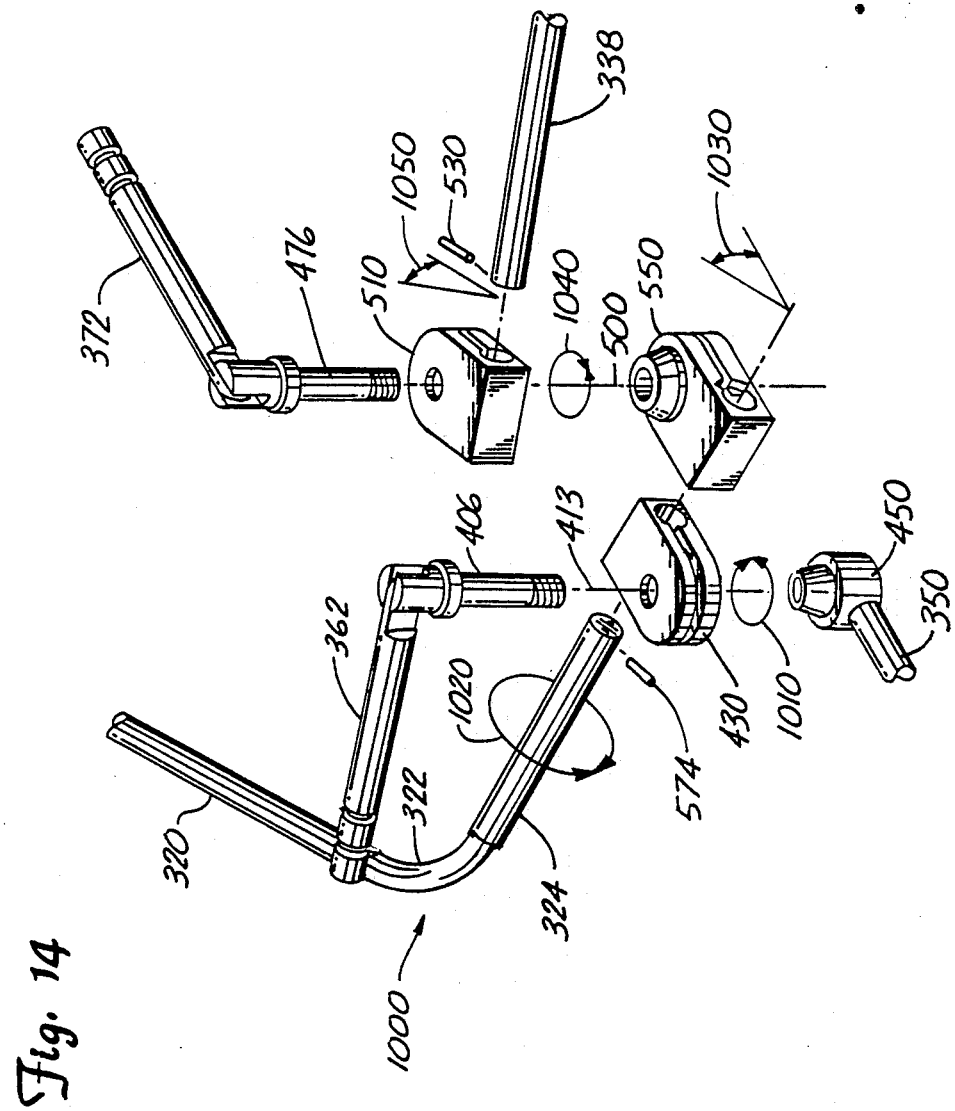
FIG. 14 is an exploded perspective view of the portion of FIG. 13 enclosed within dotted line 1000.

The alternative embodiment 310 is further illustrated in FIG. 13. The extension rod 350 supports the first clamp 360 which in turn engages the third substantially linear portion 324 of the first support rod 312. The first clamp 360 is tightened or loosened by applying force to the handle 362. A second handle retaining member 407 is in a spaced apart relationship with the first handle retaining member 408 and serves to help translate force applied to the handle 362 into rotation of the turning bolt 406, in similar fashion to that described for the bolt 476. When the first clamp 360 is loosened, the first support rod 312 has two degrees of freedom, first rotation about the pivot axis 413 of the first clamp 360 and second, rotation of the third substantially linear portion 324 of the first support rod 312 within the first clamp 360. When the handle 362 is employed to lock clamp 360, the movement of the first support rod 312 becomes locked with respect to these two degrees of freedom.

The second clamping mechanism 370 connects the second substantially linear portion 338 of the second support rod 330 to the third substantially linear portion 324 of the first support rod 312. The second clamp 370 is tightened or loosened by the handle 372. When loosened, the second clamping mechanism 370 allows three degrees of freedom to the second support rod 330 with respect to the first support rod 312. First, the clamping mechanism 370 has a limited rotation about the third substantially linear portion 324 of the first support rod 312. Second, a rotation about the pivot axis 500 is available. Third, a rotation of the second substantially linear portion 338 of the second support rod 330 within the second clamping mechanism 370 is available. When the handle 372 of the second clamping mechanism 370 is moved to a tightening or locking position, all three degrees of freedom are locked.

Thus, in the alternative embodiment 310, five degrees of freedom are available to the first support rod 312 and the second support rod 330 with respect to the extension rod 350. These five degrees of freedom may be locked by turning the handles 362 and 372.

The clamp base 450 supports the first clamping section 430 which is held in place by the turn bolt 406. The third substantially linear portion 324 is connected through the first clamping section 430 and through the lower clamping member 550. The protruding notch or pin 574 limits the rotation of the lower clamping member 550 upon the third substantially linear portion 324 within the range indicated by arrows 1030. The first clamping section 430 may rotate about pivot axis 413 on the clamp base 450 a full 360° as indicated by arrows 1010. The third substantially linear portion 324 rotates within the first clamping section 430 a full 360° as indicated by arrows 1020. The lower clamping member 550 may rotate upon the third substantially linear portion 324 a limited angle as indicated by arrows 1030 in part because of the protruding pin or notch 574. The upper clamping member 510 may rotate about the pivot axis 500 upon the lower clamping member 550 a full 360° as illustrated by arrows 1040. Finally, the second substantially linear portion 338 may rotate within the upper clamping member 510 a limited angle as illustrated by arrows 1050, due in part to the interaction of the protruding pin 530.

Turning the bolt 406 serves to lock the pivotal rotation as illustrated by arrows 1010 and the bore rotation as illustrated by arrows 1020, and is actuated by handle 362. Turning the bolt 476 serves to lock the pivotal rotation illustrated by arrows 1040 as well as the bore rotations as illustrated by arrows 1030 and 1050 and is actuated by turning the handle 372. Thus, a nearly infinite number of arrangements of the first support rod 312 and the second support rod 330 are available with respect to the extension rod 350. Once locked in position, the apparatus 310 may be used to support various retractors, in similar manner to the support apparatus 10 of FIG. 1.

Although the present invention has been described with references to preferred embodiments, workers skilled in the art will recognize that changes may be made in form and detail without departing from the spirit and scope of the invention.

What is claimed is:

1. A retractor apparatus for attaching a retractor thereto, the apparatus comprising:
   a first support rod with a first end portion;
   a second support rod with a second end portion;
   an extension rod with a third end portion;
   a first clamping means for connecting the third end portion of the extension rod to the first end portion at a first position of the first support rod, the first clamping means having both a base means portion and a first clamping section and a first force means wherein the base means portion has a first pivot bore extending therethrough with the third end portion of the extension rod attached to the base means portion wherein the base means portion has a frusto-conical section extending outwardly, the first clamping section having a first unitary body with a second pivot bore extending therethrough and a first clamping bore extending therethrough proximate one end of the first body and a slot running through the first body from the first clamping bore to an opposite end of the first body, separating the first body into first and second resilient leg portions such that when the first force means is applied to the first and second leg portions the diameter of the first clamping bore is reduced, thereby frictionally clamping the first end portion of the first support rod, the first clamping section having a frusto-conical recess such that the base means portion and the first clamping section are joined together in a frictional engagement by inserting the frusto-conical section of the base means portion into the frusto-conical recess of the first clamping section;
   a second means for connecting the first end portion at a second position of the first support rod to the second end portion of the second support rod, the second clamping means having both a second clamping section and a third clamping section and a second force means wherein the second clamping section has a second unitary body with a third pivot bore extending therethrough and a second clamping bore extending therethrough proximate one end of the second body and a slot running through the second body from the second clamping bore to an opposite end of the second body, separating the second body into third and fourth resilient leg portions such that when said second force means is applied to the leg third and fourth portions the diameter of the second clamping bore is reduced thereby frictionally clamping the first end portion of the first support rod, the second clamping section having a frusto-conical section extending outwardly; the third clamping section having a third unitary body with a fourth pivot bore extending therethrough and a third clamping bore extending therethrough proximate one end of the third body and a slot running through the third body from the third clamping bore to an opposite end of the third body, separating the third body into fifth and sixth resilient leg portions such that when said second force means is applied to the fifth and sixth leg portions the diameter of the third clamping bore is reduced, thereby frictionally clamping the second end portion of the second support rod, the third clamping section having a frusto-conical recess such that the second clamping section and the third clamping section are joined together in a frictional engagement by inserting the frusto-conical section of the second clamping section into the frusto-conical recess of the third clamping section.

2. The apparatus of claim 1 wherein the first clamping means has the first pivot bore and the second pivot bore coaxially aligned with respect to a pivot axis running through the first clamping means, the first force means includes a turning bolt extending through the pivot bores and threadably engaging the base means thereby providing a force that brings the first and second leg portions of the first clamping section together when the bolt is turned.

3. The apparatus of claim 2 wherein the turning bolt includes a head section having first and second spaced-apart handle-retaining members, each handle-retaining member having first and second pin-receiving apertures, positioned along a pin pivot axis and further including a handle having a section positionable between the first and second retaining members and having a third pin-receiving aperture alignable with the first and second pin-receiving apertures and the pivot pin insertably engaging the first, second and third apertures, such that the handle is pivotable approximately 180°.

4. The apparatus of claim 1 wherein the second clamping means has the third pivot bore and the fourth pivot bore coaxially aligned with respect to a pivot axis running through the second clamping means, the second force means includes a turning bolt extending through the pivot bores and threadably engaging the second clamping section thereby providing a force that brings the third and fourth leg portions of the second clamping section and the fifth and sixth leg portions of the third clamping section together when the bolt is turned.

5. The apparatus of claim 4 wherein the turning bolt includes a head section having first and second spaced-apart handle-retaining members, each handle-retaining member having first and second pin-receiving apertures, positioned along a pin pivot axis and further including a handle having a section positionable between the first and second retaining members and having a third pin-receiving aperture alignable with the first and second pin-receiving apertures and the pivot pin insertably engaging the first, second and third apertures, such that the handle is pivotable approximately 180°.

6. The apparatus of claim 1 wherein the first support rod has a first protruding pin extending from the first end portion at a substantially right angle.

7. The apparatus of claim 1 wherein the second support rod has a second protruding pin extending from the second end portion at a substantially right angle.

8. The apparatus of claim 6 wherein the second clamping section has a fan-shaped recess set into the second body adjoining an opening of the second clamping bore such that the first protruding pin the first support rod is disposed in the recess.

9. The apparatus of claim 7 wherein the second clamping section has a fan-shaped recess set into the third body adjoining an opening of the third clamping bore such that the second protruding pin of the second support rod is disposed in the recess.

10. A clamping mechanism comprising:
   a first rod section of a retractor apparatus having a first end with a fist pin member extending outwardly therefrom;
   a first section with a frusto-conical section extending outwardly therefrom and having a first clamping bore for frictionally engaging the first rod section and a first fan-shaped recess for receiving the first pin member thereby limiting the rotational movement of the first rod section;
   a second section having a frusto-conical recess for frictional engagement with the frusto-conical section of the first section such that when the frusto-conical section is engaged in the frusto-conical recess, the first and second sections are placed in an adjoining fashion; and
   means for providing a force to bring together the first and second sections in an adjoining fashion.

11. The clamping mechanism of claim 10 wherein the first section has a first pivot bore extending therethrough; the second secton has a second pivot bore extending therethrough; and a turning bolt extends through the first and second pivot bores and threadably engages the first section to provide a force to bring the sections together when the bolt is turned.

12. The clamping mechanism of claim 10 further including a second rod section with a second end section and a second pin member extending outwardly therefrom and wherein the second section includes a second clamping bore for frictionally engaging the second rod section and a second fan-shaped recess for receiving the second pin member thereby limiting the rotational movement of the second rod section.

13. The camping mechanism of claim 10 wherein the first fan-shaped recess has stop shoulders that define the amount of rotation of the first rod section.

14. The clamping mechanism of claim 12 wherein the second fan-shaped recess has stop shoulders that define the amount of rotation of the second rod section.

* * * * *

UNITED STATES PATENT AND TRADEMARK OFFICE
CERTIFICATE OF CORRECTION

PATENT NO. : 4,949,707
DATED : August 21, 1990
INVENTOR(S) : Bruce A. LeVahn et al.

It is certified that error appears in the above-identified patent and that said Letters Patent is hereby corrected as shown below:

Col. 16, line 15, after "second", insert --clamping--.

Col. 17, line 36, after "pin", insert --of--.

Col. 18, line 5, delete "fist", insert --first--.

Col. 18, line 23, delete "secton", insert --section--.

Col. 18, line 28, after "claim 10", insert --and--.

Col. 18, line 36, delete "camping", insert --clamping--.

Signed and Sealed this

Third Day of March, 1992

Attest:

HARRY F. MANBECK, JR.

*Attesting Officer*     *Commissioner of Patents and Trademarks*